(12) United States Patent
Davister et al.

(10) Patent No.: US 6,420,325 B2
(45) Date of Patent: *Jul. 16, 2002

(54) CHEMICAL LINKER COMPOSITIONS

(75) Inventors: Michele Davister, Liege; Guy Broze, Grace-Hollogne; Patrick Durbut, Verviers; Hoai-Chau Cao, Liege, all of (BE); Thomas Connors, Piscataway, NJ (US); John Labows, Horsham, PA (US)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/808,340

(22) Filed: Mar. 14, 2001

Related U.S. Application Data

(63) Continuation-in-part of application No. 09/566,286, filed on May 5, 2000, now abandoned, which is a continuation-in-part of application No. 09/441,907, filed on Nov. 17, 1999, now Pat. No. 6,172,032, which is a continuation-in-part of application No. 09/335,347, filed on Jun. 17, 1999, now Pat. No. 6,020,301, which is a continuation-in-part of application No. 09/164,471, filed on Oct. 1, 1998, now Pat. No. 5,955,407, which is a continuation-in-part of application No. 08/764,342, filed on Dec. 12, 1996, now Pat. No. 5,854,194.

(51) Int. Cl.$^7$ .............................. C11D 1/28; C11D 1/29; C11D 3/20; C11D 3/26
(52) U.S. Cl. .................. 510/125; 510/127; 510/137; 510/138; 510/158; 510/159; 510/101; 510/122; 510/500; 510/506
(58) Field of Search ................... 510/125, 127, 510/137, 138, 158, 159, 101, 122, 426, 432, 500, 506

(56) References Cited

U.S. PATENT DOCUMENTS

| | | | | |
|---|---|---|---|---|
| 5,043,154 A | * | 8/1991 | Gaffar et al. | 424/52 |
| 5,733,560 A | * | 3/1998 | Davister et al. | 424/407 |
| 5,736,496 A | * | 4/1998 | Durbut et al. | 510/235 |
| 5,798,330 A | * | 8/1998 | Misselyn et al. | 510/421 |
| 5,854,194 A | * | 12/1998 | Davister et al. | 510/422 |
| 5,912,222 A | * | 6/1999 | Thomas et al. | 510/417 |
| 5,955,407 A | * | 9/1999 | Davister et al. | 510/125 |
| 6,020,301 A | * | 2/2000 | Davister et al. | 510/417 |
| 6,197,732 B1 | * | 3/2001 | Davister et al. | 510/122 |

FOREIGN PATENT DOCUMENTS

| WO | WO 92/10992 | * | 9/1992 |
|---|---|---|---|

* cited by examiner

*Primary Examiner*—Gregory Delcotto
(74) *Attorney, Agent, or Firm*—Richard E. Nanfeldt

(57) ABSTRACT

A composition comprising: an organic chemical having a chemical group having a dipole moment of at least about 1.5 Debyes and a chemical linker selected from the group consisting of carboxylic acids having 4 to 6 carbon atoms, an ethoxylated polyhydric alcohol, a polyvinyl pyrrolidone and a polyethylene glycol having a molecular weight of about 600 to about 10,000, wherein the molar ratio of organic chemical to chemical linker is about 4:1 to 1:4.

1 Claim, No Drawings

CHEMICAL LINKER COMPOSITIONS

RELATED APPLICATION

This application is a continuation in part application of U.S. Ser. No. 9/566,286 filed May 5, 2000, now abandoned, which in turn is a continuation in part application of U.S. Ser. No. 9/441,907 filed Nov. 17, 1999, now U.S. Pat. No. 6,172,032, which in turn is a continuation in part application of U.S. Ser. No. 9/335,347 filed Jun. 17, 1999, now U.S. Pat. No. 6,020,301, which in turn is a continuation in part application of U.S. Ser. No. 9/164,471 filed Oct. 1, 1998, now U.S. Pat. No. 5,955,407, which in turn is a continuation in part application of U.S. Ser. No. 8/764,342 filed Dec. 12, 1996 now U.S. Pat. No 5,854,194.

FIELD OF THE INVENTION

The present invention relates to a chemical linkers that can be added to an organic chemical such as a perfume, insect repellent, antibacterial agent, and/or an allergen agent in order to reduce the rate of vaporization of the chemical additive from the surface to which it has been applied.

BACKGROUND OF THE INVENTION

A major problem is how long a chemical additive such as a perfume, fabric softener, sunscreen agent, insect repellent, antibacterial agent and/or allergen agent will be effective on a surface on which the chemical has been deposited. For example, if the lasting effect of a perfume deposited on the human skin could be increased the necessity for repeat application of the perfume would be reduced. Alternatively, if the concentration of the perfume in a solution could be reduced while maintaining its effectiveness substantial cost savings could be achieved. The present invention relates to chemical linkers which can be added to the organic chemical whereby the chemical linker by chemical association links the organic chemical to the surface on which the organic chemical has been deposited thereby decreasing the rate of vaporization of the organic chemical. The requirement of the chemical linker is that when the chemical linker is added to a organic chemical that an exothermic interaction occurs between the chemical linker and the organic chemical which causes a reduction in the active vapor pressure of the organic chemical.

The instant invention further relates to the use of the chemical linkers and the organic chemical in a surfactant based cleaning compositions.

For example, Methylneodecanamide (MNDA) is an insect repellent agent which can be added to a hard surface cleaning composition. This is necessary to deposit 10 micrograms of MNDA per cm2 to have one day efficacy. It is more than 500 molecular layers. To deliver this amount requires almost neat usage and is not compatible with consumers habits and practice. Unfortunately, one may not increase the MNDA concentration. It is desirable to increase the repellency duration without increase MNDA quantity.

On the other hand, it would be desirable to have more formulation flexibility with high oil uptake capacity perfumes. The increase of the substantivity of these perfumes ingredients would make possible to either increase performance of the perfume, or deliver the same cleaning and olfacting results with less perfume. This invention teaches that chemical linkers are a way to deliver more efficiently actives such as MNDA or perfumes to a surface to which it has been applied.

SUMMARY OF THE INVENTION

The present invention relates to chemical compositions which comprises a complex of:

(a) an organic chemical having a chemical group with a dipole moment of at least about 1.5 selected from the group consisting of a chemical compound containing an amide linkage such as an insect repellents, antibacterial agents containing a carbon-halogen bond such as triclosan, allergen agents, fabric softener or sunscreen agent containing an ester group or enzymes containing acid groups and a chemical compound containing an aldehyde group or alcohol group such as those type of compounds present in perfumes and mixtures thereof; and (b) a chemical linker which undergoes an exothermic reaction with the organic chemical, wherein the chemical linker can be a polyvinyl pyrrolidone polymer, an ethoxylated polyhydric alcohol, carboxylic acid having about 4 to about 6 carbon atoms and a polyethylene glycol having a molecular weight of about 600 to about 10,000, preferably about 1,000 to about 8,000, wherein the mole ratio of the organic chemical to the chemical linker is about 4:1 to about 1:4.

The complex of the organic chemical and chemical linker can be applied neat to the surface which is being treated, wherein the chemical linker functions to bind the organic chemical to the treated surface. Alternatively, the complex of the organic chemical and the chemical linker can be dissolved at a concentration of about 0.1 wt. % to about 99.9 wt. % in a solvent which dissolves both the chemical linker and organic chemical. Alternatively, the complex of the chemical linker and the organic chemical can be incorporated into a cleaning composition such as a body cleansing formulation, a fabric softening composition, a body lotion, a shampoo, an oral cleaning composition, a light duty liquid composition, an all purpose or microemulsion hard surface cleaning composition and a fabric care cleaning composition.

The instant invention also relates to complexes of a chemical linker, an organic chemical having a dipole moment of at least about 1.5 Debyes and an anionic sulfonate, carboxylate or sulfate containing surfactant which can be optionally mixed with a zwitterionic surfactant and an amine oxide and mixtures thereof.

DETAILED DESCRIPTION OF THE INVENTION

The present invention relates to a complex of:

(a) an organic chemical having a chemical group having a dipole moment of at least about 1.5 Debyes, more preferably at least about 1.6 Debyes; and (b) a chemical linker selected from the group consisting of carboxylic acids having 4 to 6 carbon atoms, polyethylene glycols having a molecular weight of about 600 to about 10,000, an ethoxylated polyhydric alcohol and a polyvinyl pyrrolidone, polymer wherein the mole ratio of the organic chemical to chemical linker is about 4:1 to about 1:4. The present invention also relates to a solution of 0.25 wt. % to 99.75 wt. % of the complex of the organic chemical and chemical linker in a solvent which can solubilize the complex of the organic chemical and chemical linker.

The present invention further relates to a composition which comprises approximately by weight:

(a) 0.1 to 10% of an organic chemical having a chemical group with dipole moment of at least about 1.5 Debyes, more preferably at least about 1.6 Debyes;

(b) 0 to 30% of at least one anionic surfactant having a carboxylate, sulfate or sulfonate group;

(c) 0.1 to 20% of a chemical linker compound selected from the group consisting of an ethoxylated polyhydric alcohol, a polyvinyl pyrrolidone polymer, a polyethylene glycol having a molecular weight of about 600 to 10,000 and a carboxylic acid having 4 to 6 carbon atoms and mixtures thereof, wherein the chemical linker complexes both with the anionic surfactant and the additive;

(d) 0 to 15% of a second surfactant selected from the group consisting of an amine oxide surfactant and a zwitterionic surfactant and mixtures thereof, wherein the anionic surfactant complexes with the amine oxide or zwitterionic surfactant;

(e) 0 to 20% of a cosurfactant; and (f) 5 to 99.8% of water.

The present invention relates to a body cleaning composition comprising approximately by weight:

(a) 6% to 30% of an ethoxylated $C_8$–$C_{16}$ alkyl ether sulfate;

(b) 2% to 16% of a $C_8$–$C_{16}$ alkyl sulfate or a $C_8$–$C_{16}$ alkyl benzene sulfonate;

(c) 1% to 8% of a zwitterionic surfactant or amine oxide surfactant being complexed with said sulfate and said sulfonate surfactant;

(d) 1% to 8% of a $C_{12-16}$ alkyl diethanol amide;

(e) 0.1% to 2% of a perfume;

(f) 0.5% to 6% of a chemical linker;

(g) 0.1 % to 8%, more preferably 0.2% to 8 7% of an ethoxylated or ethoxylated/propoxylated nonionic surfactant; and (h) the balance being water.

The instant compositions do not contain an organic compound containing ester groups, an anionic polycarboxylate polymer, an alkylamine, cyclomethicone, propylene glycol or an alcohol. Excluded from the instant compositions are linear molecularly dehydrated polyphosphate salts, a linear anionic polycarboxylate, N-alkyl aldonamides and alkylene carbonates.

Also excluded from the instant compositions are cosurfactants selected from the group consisting of water-soluble $C_3$–$C_4$ alkanols, polypropylene glycol of the formula $HO(CH_3CHCH_2O)_nH$ wherein n is a number from 2 to 18 and copolymers of ethylene oxide and propylene oxide and mono $C_1$–$C_6$ alkyl ethers and esters of ethylene glycol and propylene glycol having the structural formulas $R(X)_nOH$ and $R_1(X)_nOH$ wherein R is $C_1$–$C_6$ alkyl, $R_1$ is $C_2$–$C_4$ acyl group, X is $(OCH_2CH_2)$ or $(OCH_2(CH_3)CH)$ and n is a number from 1 to 4; aliphatic mono- and di-carboxylic acids containing 2 to 10 carbon atoms, preferably 3 to 6 carbons in the molecule; and triethyl phosphate.

When the mono- and di-carboxylic acid (Class 2) cosurfactants are employed in the instant microemulsion compositions at a concentration of 2 to 10 wt. %, the microemulsion compositions can be used as a cleaner for bathtubs and other hard surfaced items, which are acid resistant thereby removing lime scale, soap scum and greasy soil from the surfaces of such items damaging such surfaces. If these surfaces are zirconium white enamel, they can be damaged by these compositions.

An aminoalkylene phophoric acid at a concentration of 0.01 to 0.2 wt. % can be optionally used in conjunction with the mono- and di-carboxylic acids, wherein the aminoalkylene phosphoric acid helps prevent damage to zirconium white enamel surfaces. Additionally, 0.05 to 1 % of phosphoric acid can be used in the composition.

Representative members of the polypropylene glycol include dipropylene glycol and polypropylene glycol having a molecular weight of 200 to 1000, e.g., polypropylene glycol 400. Other satisfactory glycol ethers are ethylene glycol monobutyl ether (butyl cellosolve), diethylene glycol monobutyl ether (butyl carbitol), dipropylene glycol monomethyl ether, triethylene glycol monobutyl ether, mono, di, tri propylene glycol monobutyl ether, tetraethylene glycol monobutyl ether, propylene glycol tertiary butyl ether, ethylene glycol monoacetate and dipropylene glycol propionate.

Representative members of the aliphatic carboxylic acids include $C_3$–$C_6$ alkyl and alkenyl monobasic acids such as acrylic acid and propionic acid and dibasic acids such as glutaric acid and mixtures of glutaric acid with adipic acid and succinic acid, as well as mixtures of the foregoing acids.

While all of the aforementioned glycol ether compounds and acid compounds provide the described stability, the most preferred cosurfactant compounds of each type, on the basis of cost and cosmetic appearance (particularly odor), are diethylene glycol monobutyl ether and a mixture of adipic, glutaric and succinic acids, respectively. The ratio of acids in the foregoing mixture is not particularly critical and can be modified to provide the desired odor. Generally, to maximize water solubility of the acid mixture glutaric acid, the most water-soluble of these three saturated aliphatic dibasic acids, will be used as the major component.

Generally, weight ratios of adipic acid:glutaric acid:succinic acid is 1-3:1-8:1-5, preferably 1-2:1-6:1-3, such as 1:1:1, 1:2:1, 2:2:1, 1:2:1.5, 1:2:2, 2:3:2, etc. can be used with equally good results.

Still other classes of cosurfactant compounds providing stable microemulsion compositions at low and elevated temperatures are the mono-, di- and triethyl esters of phosphoric acid such as triethyl phosphate.

The amount of cosurfactant which might be required to stabilize the microemulsion compositions will, of course, depend on such factors as the surface tension characteristics of the cosurfactant, the type and amounds of the analephotropic complex and perfumes, and the type and amounts of any other additional ingredients which may be present in the composition and which have an influence on the thermodynamic factors enumerated above. Generally, amounts of cosurfactant in the range of from 0 to 50 wt. %, preferably from 0.1 wt. % to 25 wt. %, especially preferably from 0.5 wt. % to 15 wt. %, by weight provide such stable microemulsions for the above-described levels of primary surfactants and perfume and any other additional ingredients as described below.

As will be appreciated by the practitioner, the pH of the final microemulsion will be dependent upon the identify of the cosurfactant compound, with the choice of the cosurfactant being effected by cost and cosmetic properties, particularly odor. For example, microemulsion compositions which have a pH in the range of 1 to 10 may employ either the class 1 or the class 4 cosurfactant as the sole cosurfactant, but the pH range is reduced to 1 to 8.5 when the polyvalent metal salt is present. On the other hand, the class 2 cosurfactant can only be used as the sole cosurfactant where the product pH is below 3.2. However, where the acidic cosurfactants are employed in admixture with a glycol ether cosurfactant, compositions can be formulated at a substantially neutral pH (e.g., pH 7+−1.5, preferably 7+−0.2).

The ability to formulate neutral and acidic products without builders which have grease removal capacities is a feature of the present invention because the prior art microemulsion formulations most usually are highly alkaline or highly built or both.

The final essential ingredient in the hard surface cleaning compositions having improved interfacial tension properties is water. The proportion of water in the hard surface cleaning compositions generally is in the range of 20 wt. % to 97 wt. %, preferably 70 wt. % to 97 wt. % of the usual diluted o/w microemulsion composition.

The present invention also relates to a stable concentrated microemulsion or acidic microemulsion composition comprising approximately by weight:

(a) 3 to 40$ of an analephotropic negatively charged complex as previously herein defined;

(b) 0 to 2.5% of a fatty acid;

(c) 2 to 30% of a cosurfactant;

(d) 0.4% to 10% of a water insoluble hydrocarbon or perfume;

(e) 0 to 18% of at least one dicarboxylic acid;

(f) 0 to 1% of phosphoric acid;

(g) 0 to 0.2% of an aminoalkylene phosphoric acid;

(h) 0 to 15% of magnesium sulfate heptahydrate;

(i) 0.5% to 10% of a Lewis base, neutral polymer; and (j) the balance being water.

The instant compositions excluded the use of ethoxylated nonionic surfactants formed for the condensation product of primary or secondary alkanols and ethylene oxide or propylene oxides because the use of these ethoxylated nonionic would cause a weakening of the chemical association between the chemical linker and Lewis base and/or anionic surfactant.

The complex of the organic chemical and chemical linker can be made by simple mixing with or without heat, if the chemical linker is a liquid. If the chemical linker is a solid, the chemical linker must be heat above its melting point and the organic chemical mixed into the melted chemical linker.

The organic chemicals used in the instant invention have a chemical group having dipole moments of at least about 1.5 Debyes, more preferably at least one about 1.6 Debyes such as halogens affixed to a carbon atom, alcohol groups, aldehyde groups, ester groups, carboxylic acid groups, amine groups and amide groups. Typical chemical additives containing groups with high dipole moments are perfumes containing alcohol and aldehyde compounds, an insect repellent such as an N-lower alkyl neoalkanoamide wherein the alkyl group has 1 to 4 carbon atoms and the neodalkanoyl moiety has 7 to 14 carbon atoms, antibacterial agents such as triclosan, enzymes, proteins and an allergen such as benzyl benzoate.

As used herein and in the appended claims one of the organic chemicals is a perfume which is used in its ordinary sense to refer to and include any non-water soluble fragrant substance or mixture of substances including natural (i.e., obtained by extraction of flower, herb, blossom or plant), artificial (i.e., mixture of natural oils or oil constituents) and synthetically produced substance) odoriferous substances. Typically, perfumes are complex mixtures of blends of various organic compounds such as alcohols, aldehydes, ethers, aromatic compounds and varying amounts of essential oils (e.g., terpenes) such as from 0% to 80%, usually from 10% to 70% by weight. The essential oils themselves are volatile odoriferous compounds and also serve to dissolve the other components of the perfume.

The analephotropic negatively charged anionic complex which can be contained in the instant cleaning compositions such as a fabric cleaning composition, a light duty liquid composition, an all purpose or microemulsion composition, a body cleaning composition or a shampoo comprises a complex of:

(a) at least one anionic surfactant which is an alkali metal salt or an alkaline earth metal salt of a sulfonate or sulfate surfactant; and (b) an amine oxide or zwitterionic surfactant wherein the ratio of the anionic surfactant to the amine oxide surfactantr zwitterionic surfactant is 7:1 to 0.2:1, more preferably 2:1 to 0.4:1. The instant composition contains about 3 to about 40 wt. %, more preferably about 5 to about 20 wt. %, of the analephotropic negatively charged complex.

Suitable water-soluble non-soap, anionic surfactants include those surface-active or detergent compounds which contain an organic hydrophobic group containing generally 8 to 26 carbon atoms and preferably 10 to 18 carbon atoms in their molecular structure and at least one water-solubilizing group selected from the group of sulfonate, sulfate and carboxylate so as to form a water-soluble detergent. Usually, the hydrophobic group will include or comprise a $C_8$–$C_{22}$ alkyl, alkyl or acyl group. Such surfactants are employed in the form of water-soluble salts and, the salt-forming cation usually is selected from the group consisting of sodium, potassium, or magnesium, with the sodium and magnesium cations again being preferred.

Examples of suitable sulfonated anionic surfactants are the well known higher alkyl mononuclear aromatic sulfonates such as the higher alkyl benzene sulfonates containing from 10 to 16 carbon atoms in the higher alkyl group in a straight or branched chain, $C_8$–$C_{15}$ alkyl toluene sulfonates and $C_8$–$C_{15}$ alkyl phenol sulfonates.

A preferred sulfonate is linear alkyl benzene sulfonate having a high content of 3- (or higher) phenyl isomers and a correspondingly low content (well below 50%) of 2-(or lower) phenyl isomers, that is, wherein the benzene ring is preferably attached in large part at the 3 or higher (for example, 4, 5, 6 or 7) position of the alkyl group and the content of the isomers in which the benzene ring is attached in the 2 or 1 position is correspondingly low. Particularly preferred materials are set forth in U.S. Pat. No. 3,320,174.

Other suitable anionic surfactants are the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, preferably 12 to 21 carbon atoms, and having the formula $RCH=CHR_1$ where R is a higher alkyl group of 6 to 23 carbons and $R_1$ is an alkyl group of 1 to 17 carbons or hydrogen to form a mixture of sultones and alkene sulfonic acids which is then treated to convert the sultones to sulfonates. Preferred olefin sulfonates contain from 14 to 16 carbon atoms in the R alkyl group and are obtained by sulfonating an a-olefin.

Other examples of suitable anionic sulfonate surfactants are the paraffin sulfonates containing 10 to 20, preferably 13 to 17, carbon atoms. Primary paraffin sulfonates are made by reacting long-chain alpha olefins and bisulfites and paraffin sulfonates having the sulfonate group distributed along the paraffin chain are shown in U.S. Pat. Nos.. 2,503,280; 2,507,088; 3,260,744; 3,372,188; and German Patent 735, 096.

Examples of satisfactory anionic sulfate surfactants are the $C_8$–$C_{18}$ alkyl sulfate salts and the ethoxylated $C_8$–$C_{18}$ alkyl ether sulfate salts having the formula $R(OC_2H_4)_n OSO_3M$ wherein n is 1 to 12, preferably 1 to 5, and M is a metal cation selected from the group consisting of sodium, potassium, ammonium, magnesium and mono-, di- and triethanol ammonium ions. The alkyl sulfates may be obtained by sulfating the alcohols obtained by reducing glycerides of coconut oil or tallow or mixtures thereof and neutralizing the resultant product.

On the other hand, the ethoxylated alkyl ether sulfates are obtained by sulfating the condensation product of ethylene oxide with a $C_8$–$C_{18}$ alkanol and neutralizing the resultant product. The alkyl sulfates may be obtained by sulfating the alcohols obtained by reducing glycerides of coconut oil or tallow or mixtures thereof and neutralizing the resultant product. The ethoxylated alkyl ether sulfates differ from one another in the number of moles of ethylene oxide reacted with one mole of alkanol. Preferred alkyl sulfates and preferred ethoxylated alkyl ether sulfates contain 10 to 16 carbon atoms in the alkyl group.

The ethoxylated $C_8$–$C_{12}$ alkylphenyl ether sulfates containing from 2 to 6 moles of ethylene oxide in the molecule also are suitable for use in the inventive compositions. These surfactants can be prepared by reacting an alkyl phenol with 2 to 6 moles of ethylene oxide and sulfating and neutralizing the resultant ethoxylated alkylphenol.

Other suitable anionic surfactants are the $C_9$–$C_{15}$ alkyl ether polyethenoxyl carboxylates having the structural formula $R(OC_2H_4)_nOX$ COOH wherein n is a number from 4 to 12, preferably 5 to 10 and X is selected from the group consisting of $CH_2$, $(C(O)R_1$ and

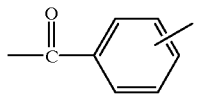

wherein $R_1$ is a $C_1$–$C_3$ alkylene group. Preferred compounds include $C_9$-$C_{11}$ alkyl ether polyethenoxy (7–9) C(O) $CH_2CH_2COOH$, $C_{13}$–$C_{15}$ alkyl ether polyethenoxy (7–9)

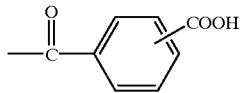

and $C_{10}$–$C_{12}$ alkyl ether polyethenoxy (5–7) $CH_2COOH$. These compounds may be prepared by reacting ethylene oxide with appropriate alkanol and reacting this reaction product with chloracetic acid to make the ether carboxylic acids as shown in U.S. Pat. No. 3,741,911 or with succinic anhydride or phthalic anhydride. Obviously, these anionic surfactants will be present either in acid form or salt form depending upon the pH of the final composition, with salt forming cation being the same as for the other anionic surfactants.

Of the foregoing non-soap anionic surfactants used in forming the analephotropic complex, the preferred surfactants are the sodium or magnesium salts of the $C_8$–$C_{18}$ alkyl sulfates such as magnesium lauryl sulfate and sodium lauryl sulfate and mixtures thereof.

Generally, the proportion of the nonsoap-anionic surfactant will be in the range of 0 to 30%, preferably from 1% to 15%, by weight of the cleaning composition.

The instant composition contains as part of the analephotropic negatively charged complex about 3% to about 30%, preferably about 4% to about 15% of an amine oxide, or zwitterionic surfactant.

The amine oxides used in forming the analephotropic complex are depicted by the formula

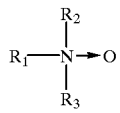

wherein $R_1$ is a $C_{10}$–$C_{18}$ a linear or branched chain alkyl group, $R_2$ is a $C_1$–$C_{16}$ linear alkyl group and $R_3$ is a $C_1$–$C_{16}$ linear alkyl group.

The zwitterionic surfactant used in forming the analephotropic complex is a water soluble betaine having the general formula:

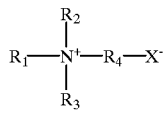

wherein $X^-$ is selected from the group consisting of $COO^-$ and $SO_{3-}$ and $R_1$ is an alkyl group having 10 to about 20 carbon atoms, preferably 12 to 16 carbon atoms, or the amido radical:

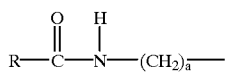

wherein R is an alkyl group having about 9 to 19 carbon atoms and a is the integer 1 to 4: $R_2$ and $R_3$ are each alkyl groups having 1 to 3 carbons and preferably 1 carbon; $R_4$ is an alkylene or hydroxyalkylene group having from 1 to 4 carbon atoms and, optionally, one hydroxyl group. Typical alkyldimethyl betaines include decyl dimethyl betaine or 2-(N-decyl-N, N-dimethyl-ammonia) acetate, coco dimethyl betaine or 2-(N-coco N, N-dimethylammonia) acetate, myristyl dimethyl betaine, palmityl dimethyl betaine, lauryl dimethyl betaine, cetyl dimethyl betaine, stearyl dimethyl betaine, etc. The amidobetaines similarly include cocoamidoethylbetaine, cocoamidopropyl betaine and the like. A preferred betaine is coco ($C_8$–$C_{18}$) amidopropyl dimethyl betaine. Three preferred betaine surfactants are GENAGEN CAB™ and REWOTERIC AMB 13198 and GOLMSCHMIDT BETAINE L7™.

The instant compositions contain about 0.5 wt. % to about 10 wt. %, more preferably about 1 wt. % to about 7.0 wt. %, of a chemical linker which can be a carboxylic acid having 4 to 6 carbon atoms, a Lewis base, neutral polymer which is soluble in water and has either a nitrogen or oxygen atom with a pair of free electrons such that the Lewis base, neutral polymer can electronically associate with the anionic surfactant and an active organic chemical having a dipole moment of at least about 1.5 Debyes such as an enzyme, protein, allergen agent, a perfume or an antimicrobial agent such as triclosan or an insect repellent such as MNDA wherein the Lewis base, neutral polymer is deposit and anchors onto the surface of the surface being treated thereby holding the organic chemical in close proximity to the surface thereby ensuring that the properties being parted by the organic chemical last longer. The chemical linker can also link with the anionic surfactant to hold the anionic surfactant in close proximity to the surface being cleaned.

The Lewis base, neutral polymers are selected from the group consisting of an ethoxylated polyhydric alcohol, a polyvinyl pyrrolidone polymer and a polyethylene glycol.

The ethoxylated polyhydric alcohol is depicted by the following formula:

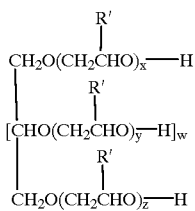

wherein w equals one to four and x, y and z have a value between 0 and 60, more preferably 0 to 40, provided that (x+y+z) equals about 2 to about 100, preferably about 4 to about 24, and most preferably about 4 to about 19, and wherein R' is either hydrogen atom or methyl group. A preferred ethoxylated polyhydric alcohol is glycerol 6EO.

The polyvinyl pyrrolidone polymer is depicted by the formula:

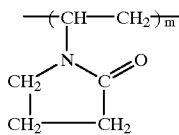

wherein m is about 20 to about 350, more preferably about 70 to about 110.

The polyethylene glycol is depicted by the formula

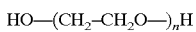

wherein n is about 8 to about 225, more preferably about 10 to about 100,000, wherein PEG1000 is preferred which is a polyethylene glycol having a molecular weight of about 1000.

The ethoxylated nonionic surfactant is present in amounts of about 0.1% to 8%, preferably 0.2 to 7% by weight of the composition and provides superior performance in the removal of oily soil and mildness to human skin.

The water soluble nonionic surfactants utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing 8 to 18 carbon atoms in a straight or branched chain configuration) condensed with 5 to 30 moles of ethylene oxide, for example, lauryl or myristyl alcohol condensed with 16 moles of ethylene oxide (EO), tridecanol condensed with 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to 14 carbon atoms in length and wherein the condensate contains either 6 moles of EO per mole of total alcohol or 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohols containing about 9-15 carbon atoms, such as $C_9$–$C_{11}$ alkanol condensed with 8 moles of ethylene oxide (Neodol 91-8), $C_{12-13}$ alkanol condensed with 6.5 moles ethylene oxide (Neodol 23-6.5), $C_{12-15}$ alkanol condensed with 12 moles ethylene oxide (Neodol 25-12), $C_{14-15}$ alkanol condensed with 13 moles ethylene oxide (Neodol 45-13), and the like. Such ethoxamers have an HLB (hydrophobic lipophilic balance) value of 8–15 and give good/W emulsification, whereas ethoxamers with HLB values below 8 contain less than 5 ethyleneoxy groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from 8 to 18 carbon atoms in a straight- or branched chain alkyl group with 5 to 30 moles of ethylene oxide. Specific examples of alkyl phenol ethoxylates include nonyl condensed with 9.5 moles of EO per mole of nonyl phenol, dinonyl phenol condensed with 12 moles of EO per mole of phenol, dinonyl phenol condensed with 15 moles of EO per mole of phenol and di-isoctylphenol condensed with 15 moles of EO per mole of phenol. Commercially available nonionic surfactants of this type include Igepal CO-630 (nonyl phenol ethoxylate) marketed by GAF Corporation.

Also among the satisfactory nonionic detergents are the water-soluble condensation products of a $C_8$–$C_{20}$ alkanol with a heteric mixture of ethylene oxide and propylene oxide wherein the weight ratio of ethylene oxide to propylene oxide is from 2.5:1 to 4:1, preferably 2.8:1-3.3:1, with the total of the ethylene oxide and propylene oxide (including the terminal ethanol or propanol group) being from 60–85%, preferably 70–80%, by weight. Such detergents are commercially available from BASF-Wyandotte and a particularly preferred detergent is a $C_{10}$–$C_{16}$ alkanol condensate with ethylene oxide and propylene oxide, the weight ratio of ethylene oxide to propylene oxide being 3:1 and the total alkoxy content being 75% by weight.

Other suitable water-soluble nonionic detergents which are less preferred are marketed under the trade name "Pluronics." The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L62 and L64.

The liquid body cleaning compositions of this invention may, if desired, also contain other components either to provide additional effect or to make the product more attractive to the consumer. The following are mentioned by way of example: Colors or dyes in amounts up to 0.5% by weight; bactericides in amounts up to 1% by weight; preservatives or antioxidizing agents, such as formalin, 5-chloro-2-methyl-4-isothaliazolin-3-one, 2,6-di-tert.butyl-p-cresol, etc., in amounts up to 2% by weight; and pH adjusting agents, such as sulfuric acid or sodium hydroxide, as needed. Furthermore, if opaque compositions are desired, up to 4% by weight of an opacifier may be added.

The body cleaning compositions are directly ready for use or can be diluted as desired and in either case no or only minimal rinsing is required and substantially no residue or streaks are left behind. When intended for use in the neat form, the liquid compositions can be packaged under pressure in an aerosol container or in a pump-type sprayer for the so-called spray-and-wipe type of application.

Because the body cleaning compositions as prepared are aqueous liquid formulations and since no particular mixing is required to form the all purpose cleaning or microemulsion composition, the compositions are easily prepared simply by combining all the ingredients in a suitable vessel or container. The order of mixing the ingredients is not particularly important and generally the various ingredients can be added sequentially or all at once or in the form of aqueous solutions of each or all of the primary detergents can be separately prepared and combined with each other and with the perfume.

The following examples illustrate the complexes of additives and chemical linker and liquid cleaning compositions containing complexes of the chemical linker with the additive and/or surfactant invention. Unless otherwise specified, all percentages are by weight. The exemplified compositions are illustrative only and do not limit the scope of the invention. Unless otherwise specified, the proportions in the examples and elsewhere in the specification are by weight.

EXAMPLE I

The following complexes of chemical additive and chemical linker were made:

Tests were run with a microcalorimeter CALVET. A cell contains 0.5 g of the chemical additive and 0.5 g of a chemical linker such as polyethylene glycol in two separated parts. A semi circular cup disposed with in the cell allows the mixing of the two components in the cell. The heat flow generated by the mixing is measured. If the components interact together, their mixing releases heat. The table hereafter gives the components of the mixture, the time and the microwatt value to the maximum of the exothermic peak.

|  | A | B | C | D | E | F | G | H | I | J |
|---|---|---|---|---|---|---|---|---|---|---|
| Chemical additives |  |  |  |  |  |  |  |  |  |  |
| Quat ester | 0.5 |  |  |  |  |  |  |  |  |  |
| Benzyl benzoate |  | 0.5 |  |  |  |  |  |  |  |  |
| Dihydromyrcenol - Perfume |  |  | 0.5 |  |  |  |  |  |  |  |
| Aldehyde C9 - Perfume |  |  |  | 0.5 |  |  |  |  | 0.5 |  |
| Triclosan |  |  |  |  | 0.5 |  |  |  |  |  |
| MNDA |  |  |  |  |  | 0.5 |  |  |  | 1.5 |
| n-dimethyl para-amine octyl benzoate |  |  |  |  |  |  | 0.5 |  |  |  |
| BSA - Protein |  |  |  |  |  |  |  | 0.5 |  |  |
| PEG 200 |  |  |  | 0.5 |  |  |  |  |  |  |
| PEG 600 | 0.5 | 0.5 |  |  | 0.5 |  |  | 0.5 |  |  |
| PEG 6000 |  |  | 0.5 |  |  | 0.5 | 0.5 |  |  |  |
| Exothermic reaction |  |  |  |  |  |  |  |  |  |  |
| Microwatte to exothermic energy peak | 1070 | 3240 | 115 | 55500 | 327 | 171 | 98 | 700 | 39700 | 1934 |
| Time (seconds) to energy peak | 80 | 130 | 30 | 40 | 120 | 130 | 140 | 820 | 380 | 670 |
| LEVENOL F200 ™ |  |  |  |  |  |  |  |  | 0.5 |  |
| Isobutyric Acid |  |  |  |  |  |  |  |  |  | 0.3 |

EXAMPLE II

The following formulas were made by simple mixing at 25° C. and tested for roach repelling.

|  | Weight Percent | | | | |
|---|---|---|---|---|---|
|  | A | B | C | D | E |
| Deionized Water | 82.2260 | 83.2260 | 82.9260 | 84.9260 | 83.9260 |
| MgSO4·7H20 | 1.0000 | 1.0000 | 1.0000 | 1.0000 | 1.0000 |
| $C_{14-17}$ Paraffin Sulfonate 60% No P | 6.6700 | 6.6700 | 6.6700 | 6.6700 | 6.6700 |
| $C_{13-15}$ Fatty Alcohol EO 7:1/PO 4:1 | 3.0000 | 3.0000 | 0.0000 | 0.0000 | 0.0000 |
| Esterified Polyethoxyether Levanol F200 | 0.0000 | 0.0000 | 2.3000 | 2.3000 | 2.3000 |
| PEG-600 | 0.0000 | 1.0000 | 0.0000 | 0.0000 | 1.0000 |
| Diethylene Glycol Monobutyl Ether | 3.5000 | 2.5000 | 3.5000 | 2.5000 | 2.5000 |
| Sodium Hydroxide (38% Na2O) | 0.0500 | 0.0500 | 0.0500 | 0.0500 | 0.0500 |

-continued

|  | Weight Percent | | | | |
| --- | --- | --- | --- | --- | --- |
|  | A | B | C | D | E |
| Dist. Coco Fatty Acid | 0.5000 | 0.5000 | 0.5000 | 0.5000 | 0.5000 |
| Stabilisant B 30% | 0.1540 | 0.1540 | 0.1540 | 0.1540 | 0.1540 |
| FD&C Green 3 Cl42053 | 0.0700 | 0.0700 | 0.0700 | 0.0700 | 0.0700 |
| FD&C Yellow 10 Cl 47005 | 0.0300 | 0.0300 | 0.0300 | 0.0300 | 0.0300 |
| Repellent Perfume - Mizqui | 0.8000 | 0.8000 | 0.8000 | 0.8000 | 0.8000 |
| Methyl Neodecanamide | 2.0000 | 1.0000 | 2.0000 | 1.0000 | 1.0000 |
| Days Roach Repellency, Probit 90% | 7.1000 | 1.7000 | 10.9000 | 8.8000 | 7.3000 |

The testing for roach repellency was done by a tile cup test procedure which was as follows:

German cockroaches (*Blattella germancia*) were maintained at 27° C. on a 12 hour light/12 hour dark photo period. Vinyl floors were cleaned and cut into 3×3 inch squares (58.1 cm²) with an electric saw. A 1.5 cm square notch was cut out of half of the resulting squares to provide the roaches access to the shelter. The tiles were washed with water before treatment. Each of six cut tiles (two with access openings) were treated with 0.62 ml of test product (Formula L) diluted 4:1. Similarly six control tiles were treated with 0.62 ml of an identical formulation which did not contain MNDA (Formula M) diluted 4:1. The tiles were allowed to dry 4-6 hours before the cup, a six sided cube was assembled. The cut tiles were held together firmly with strips of clear tape on the outside edges, except the floor of the shelter was left unattached. The control and product treated shelter were placed in the cage and the bioassay started. Forty-eight hours prior to initiation of the assay, 50 male German cockroaches were allowed to acclimate to the plastic test cages (51×28×20 cm) with food and water available in the center, outside of the cups. A thin film of Teflon emulsion on the sides of the cages restricted the insects to the floor of the cage.

The number of insects resting on the inner walls of each cup were recorded in the middle of the photophase daily for 14 days or until equal numbers were found in treated and control cups. After counting, all roaches were removed from each cup. The position of the cups were reversed each day.

Repellency was calculated as:

$$\text{Repellency} = 100 \frac{N_t}{N_t + N_c}$$

where $N_t$ is the number of insects on the treated surface and $N_c$ is the number on the control surface. Any insect found outside of either shelter was not counted. Generally, less than 5 of the 50 insects were found outside of the shelters.

What is claimed is:

1. A body cleaning composition comprises approximately by weight:
   (a) 6% to 30% of an ethoxylated $C_8$–$C_{16}$ alkyl ether sulfate;
   (b) 2% to 16% of a $C_8$–$C_{16}$ alkyl sulfate or a $C_8$–$C_{16}$ alkyl benzene sulfonate;
   (c) 1% to 8% of a zwitterionic surfactant being complexed with said sulfate and said sulfonate surfactant;
   (d) 1% to 8% of a $C_{12\text{-}16}$ alkyl diethanol amide;
   (e) 0.1% to 2% of a perfume;
   (f) 0.5% to 6% of a chemical linker being selected from the group consisting of a polyvinyl pyrrolidone polymer, an ethoxylated polyhydric alcohol, a carboxylic acid having about 4 to about 6 carbon atoms and a polyethylene glycol having a molecular weight of about 600 to about 10,000;
   (g) 0.1% to 7% of an ethoxylated nonionic surfactant; and
   (h) the balance being water wherein the composition excludes the presence of an organic compound containing ester groups, an anionic polycarboxylate polymer, an alkylamine, cyclomethicone, propylene glycol, linear molecularly dehydrated polyphosphate salts, N-alkyl aldonamides, alkylene carbonates, water soluble $C_3$–$C_4$ alkanols, polypropylene glycol of the formula $HO(CH_3CHCH_2O)_nH$ wherein n is a number from 2 to 18, copolymers of ethylene oxide and propylene oxide, mono $C_1$–$C6$ alkyl ethers and esters of ethylene glycol and propylene glycol having the structural formulas R(x)nOH and R1(X)nOH wherein R is C1–C6 alkyl, R1 is C2–C4 acyl group, X is (OCH2CH2) or (OCH2(CH3)CH) and n is a number from 1 to 4; aliphatic mono- and di-carboxylic acids containing 2 to 10 carbon atoms, and triethyl phosphate.

\* \* \* \* \*